(12) United States Patent
Salmisuo et al.

(10) Patent No.: US 8,764,975 B2
(45) Date of Patent: Jul. 1, 2014

(54) SOLIDS SEPARATOR AND METHOD OF TREATMENT FOR BIOWASTE

(75) Inventors: Mauri Salmisuo, Tuusula (FI); Juha Mattila, Porvoo (FI); Teppo Nurminen, Ojakkala (FI)

(73) Assignee: Steris Europe, Inc. Suomen Sivuliike, Tuusula (FI)

( * ) Notice: Subject to any disclaimer, the term of this patent is extended or adjusted under 35 U.S.C. 154(b) by 0 days.

(21) Appl. No.: 13/444,185

(22) Filed: Apr. 11, 2012

(65) Prior Publication Data

US 2012/0267323 A1    Oct. 25, 2012

(30) Foreign Application Priority Data

Apr. 12, 2011   (FI) .................................... 20115350

(51) Int. Cl.
*A61L 11/00*   (2006.01)
*A61L 2/07*    (2006.01)

(52) U.S. Cl.
USPC ........... 210/104; 210/108; 210/109; 210/184; 210/205; 210/232; 210/411; 210/742; 210/744; 210/774; 422/26; 422/105; 422/106; 422/108; 422/255; 422/260; 588/312; 588/405

(58) Field of Classification Search
None
See application file for complete search history.

(56) References Cited

U.S. PATENT DOCUMENTS

| | | | |
|---|---|---|---|
| 2,432,317 A * | 12/1947 | Lawson et al. ................... | 210/93 |
| 2,651,414 A * | 9/1953 | Lawson ......................... | 210/307 |
| 3,700,468 A | 10/1972 | Shore et al. | |
| 4,009,104 A * | 2/1977 | Behrendt et al. .............. | 210/744 |
| 4,089,781 A * | 5/1978 | Asp ............................... | 210/797 |
| 4,108,601 A * | 8/1978 | Wolff ............................ | 422/295 |
| 4,160,647 A * | 7/1979 | Sendov et al. ................ | 422/106 |
| 4,164,538 A * | 8/1979 | Young et al. ................... | 422/26 |
| 4,166,096 A * | 8/1979 | Gillis et al. .................... | 422/119 |
| 4,203,943 A * | 5/1980 | Gillis et al. .................... | 422/27 |
| 4,203,947 A * | 5/1980 | Young et al. .................. | 422/114 |
| 4,239,730 A * | 12/1980 | Fahlvik et al. ................ | 422/109 |
| 4,239,731 A * | 12/1980 | Gillis et al. .................... | 422/112 |
| 4,284,600 A * | 8/1981 | Gillis et al. ..................... | 422/26 |
| 4,592,847 A * | 6/1986 | Schumacher ................. | 210/770 |
| 4,710,350 A * | 12/1987 | Petersen ......................... | 422/37 |
| RE32,695 E * | 6/1988 | Nahra et al. .................. | 261/118 |
| 5,091,158 A * | 2/1992 | Drauschke et al. ........... | 422/295 |
| 5,114,596 A * | 5/1992 | Laterra ......................... | 210/798 |

(Continued)

FOREIGN PATENT DOCUMENTS

DE    3338572    5/1985   ............ B01D 29/01

OTHER PUBLICATIONS

EPO Form 1570N—Search Report from corresponding European Patent App. No. 12397513.8; 5 pages.

*Primary Examiner* — Robert James Popovics
(74) *Attorney, Agent, or Firm* — Kusner & Jaffe; Michael A. Centanni

(57) ABSTRACT

The invention relates to a device and a method for the separation of solids from a biowaste slurry before heat treatment, and for heat treatment of the separated solids. The device comprises a chamber with a main inlet port for feeding slurry, and outlet ports. A unit for separating solids is adapted to an outlet port so, that liquid leaving the chamber has passed through the separation unit. A second outlet port is provided directly from the chamber to allow removal, following sterilization, of solids collected in the chamber. The sterilization is secured by temperature monitoring at representative locations.

4 Claims, 1 Drawing Sheet

(56) References Cited

U.S. PATENT DOCUMENTS

| | | | |
|---|---|---|---|
| 5,132,084 A * | 7/1992 | Harrell et al. | 422/26 |
| 5,217,688 A * | 6/1993 | Von Lersner | 422/26 |
| 5,332,532 A * | 7/1994 | Kaye et al. | 588/16 |
| 5,364,589 A * | 11/1994 | Buehler et al. | 422/26 |
| 5,384,092 A * | 1/1995 | Sawhill et al. | 422/32 |
| 5,454,953 A * | 10/1995 | Waibel | 210/664 |
| 5,480,610 A * | 1/1996 | Birkholz et al. | 422/26 |
| 5,540,846 A * | 7/1996 | Koch et al. | 210/741 |
| 5,547,582 A * | 8/1996 | Waibel | 210/664 |
| 5,628,916 A * | 5/1997 | Stevens et al. | 210/798 |
| 5,666,878 A * | 9/1997 | Taricco | 100/73 |
| 5,687,755 A * | 11/1997 | Farquhar et al. | 137/182 |
| 5,759,491 A * | 6/1998 | Bunin | 422/38 |
| 5,799,883 A * | 9/1998 | Lewis et al. | 241/21 |
| 5,880,438 A * | 3/1999 | Parrini et al. | 219/519 |
| 5,906,800 A * | 5/1999 | Napierkowski et al. | 422/298 |
| 5,945,006 A * | 8/1999 | Mignani | 210/774 |
| 5,997,733 A * | 12/1999 | Wilbur et al. | 210/85 |
| 5,997,813 A * | 12/1999 | Yaskoff et al. | 422/26 |
| 6,036,862 A * | 3/2000 | Stover | 210/603 |
| 6,097,015 A * | 8/2000 | McCullough et al. | 219/686 |
| 6,113,854 A * | 9/2000 | Milum et al. | 422/32 |
| 6,180,070 B1 * | 1/2001 | Benson | 422/295 |
| 6,332,977 B1 * | 12/2001 | Janecek | 210/96.1 |
| 6,379,613 B1 * | 4/2002 | Stempf | 422/26 |
| 6,437,211 B2 * | 8/2002 | Kaye et al. | 588/318 |
| 6,472,580 B2 * | 10/2002 | Kaye et al. | 588/317 |
| 6,521,135 B1 * | 2/2003 | Benesi | 210/771 |
| 6,660,164 B1 * | 12/2003 | Stover | 210/612 |
| 6,886,698 B2 * | 5/2005 | Tully | 210/452 |
| 6,890,129 B2 * | 5/2005 | Fabbri | 406/106 |
| 6,926,874 B2 * | 8/2005 | Ongaro | 422/298 |
| 6,959,504 B2 * | 11/2005 | Fabbri | 34/380 |
| 7,011,741 B2 * | 3/2006 | Benesi | 210/97 |
| 7,183,453 B2 * | 2/2007 | Wilson et al. | 588/318 |
| 7,211,229 B2 * | 5/2007 | Halli | 422/307 |
| 7,381,323 B2 * | 6/2008 | Umezawa et al. | 210/108 |
| 7,445,716 B2 * | 11/2008 | Quintel et al. | 210/636 |
| 7,497,340 B2 * | 3/2009 | Hershberger et al. | 210/435 |
| 7,611,604 B2 * | 11/2009 | Salmisuo et al. | 159/49 |
| 7,621,898 B2 * | 11/2009 | Lalomia et al. | 604/319 |
| 7,641,852 B1 * | 1/2010 | McPhail et al. | 422/26 |
| 7,812,206 B2 * | 10/2010 | Wilsak et al. | 585/814 |
| 7,815,808 B2 * | 10/2010 | Benesi et al. | 210/741 |
| 7,829,755 B2 * | 11/2010 | Wilson et al. | 588/319 |
| 7,857,980 B2 * | 12/2010 | Bellussi | 210/742 |
| 7,910,788 B2 * | 3/2011 | Wilson et al. | 588/318 |
| 8,066,953 B2 * | 11/2011 | Muth | 422/198 |
| 8,201,695 B2 * | 6/2012 | Kang et al. | 210/350 |
| 8,206,660 B2 * | 6/2012 | Buczynski et al. | 422/296 |
| 8,211,319 B2 * | 7/2012 | Wilsak et al. | 210/767 |
| 8,309,711 B2 * | 11/2012 | Wiley | 536/127 |
| 8,409,429 B2 * | 4/2013 | Kaske | 210/86 |
| 8,470,182 B2 * | 6/2013 | Muth | 210/749 |
| 2001/0009969 A1 * | 7/2001 | Kaye et al. | 588/205 |
| 2001/0053869 A1 * | 12/2001 | Kaye et al. | 588/200 |
| 2003/0007914 A1 * | 1/2003 | Ongaro | 422/292 |
| 2003/0007915 A1 * | 1/2003 | Ongaro | 422/297 |
| 2003/0040651 A1 * | 2/2003 | Wilson et al. | 585/240 |
| 2004/0018112 A1 * | 1/2004 | Wilson et al. | 422/3 |
| 2004/0026312 A1 * | 2/2004 | Tully | 210/452 |
| 2004/0168986 A1 * | 9/2004 | Katano | 210/695 |
| 2004/0208784 A1 * | 10/2004 | Matsuda et al. | 422/38 |
| 2005/0002824 A1 * | 1/2005 | Halli et al. | 422/3 |
| 2005/0145567 A1 * | 7/2005 | Quintel et al. | 210/636 |
| 2005/0189303 A1 * | 9/2005 | Kaeske | 210/774 |
| 2006/0027509 A1 | 2/2006 | Benesi et al. | 210/770 |
| 2006/0102292 A1 * | 5/2006 | Salmisuo et al. | 159/49 |
| 2006/0222574 A1 * | 10/2006 | Kaye et al. | 422/184.1 |
| 2006/0247485 A1 * | 11/2006 | Wilson et al. | 588/299 |
| 2007/0038013 A1 * | 2/2007 | Wilson et al. | 588/318 |
| 2007/0175825 A1 * | 8/2007 | Denney | 210/631 |
| 2007/0199903 A1 * | 8/2007 | Denney | 210/723 |
| 2007/0218541 A1 * | 9/2007 | Denney et al. | 435/267 |
| 2007/0221552 A1 * | 9/2007 | Denney | 210/85 |
| 2008/0078726 A1 * | 4/2008 | Pancaldi et al. | 210/770 |
| 2008/0138253 A1 * | 6/2008 | Golder et al. | 422/112 |
| 2009/0050581 A1 * | 2/2009 | Kaske | 210/797 |
| 2009/0101601 A1 * | 4/2009 | Kaske | 210/798 |
| 2009/0105517 A1 * | 4/2009 | Kaye et al. | 588/318 |
| 2009/0137858 A1 * | 5/2009 | Wilson et al. | 588/318 |
| 2011/0031192 A1 * | 2/2011 | Wiley | 210/770 |
| 2011/0040138 A1 * | 2/2011 | Wilson et al. | 588/317 |
| 2011/0048086 A1 * | 3/2011 | Kaye et al. | 71/14 |
| 2011/0171073 A1 * | 7/2011 | Wilson et al. | 422/108 |
| 2012/0059603 A1 * | 3/2012 | Stering | 702/47 |
| 2012/0267323 A1 * | 10/2012 | Salmisuo et al. | 210/766 |
| 2012/0301356 A1 * | 11/2012 | Olson et al. | 422/33 |
| 2013/0084225 A1 * | 4/2013 | Buczynski | 422/292 |
| 2013/0236392 A1 * | 9/2013 | Naterer et al. | 423/648.1 |
| 2014/0037495 A1 * | 2/2014 | Ahiska et al. | 422/3 |

* cited by examiner

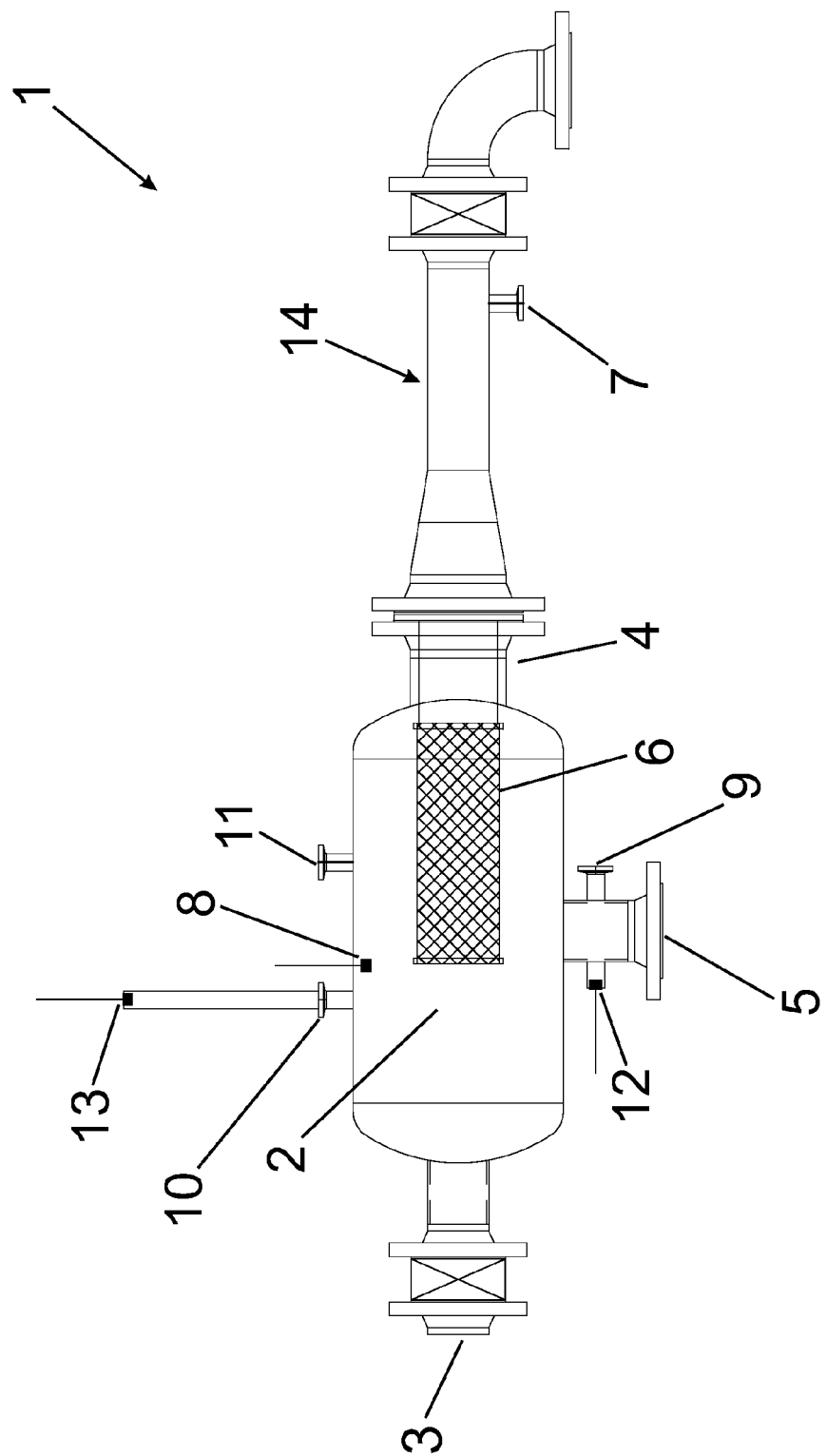

SOLIDS SEPARATOR AND METHOD OF TREATMENT FOR BIOWASTE

FIELD OF THE INVENTION

The invention relates to the field of sterilization of biological waste. More particularly, the invention relates to a device and a method for the separation of solids from a slurry before heat treatment, and for heat treatment of the separated solids.

BACKGROUND OF THE INVENTION

Biological waste in the form of liquids and suspensions is produced e.g. in hospitals, agricultural or biological research and production facilities, plasma fractionation facilities, etc. Biological wastes produced in such facilities cannot be directly conducted to a sewer system, as these wastes often contain micro-organisms, such as bacteria, viruses, germs and the like, which are hazardous to humans and animals. Prior to conducting to a sewer system, such biowaste must first be deactivated in a treatment plant designed for this purpose. For the treatment of biowaste, different treatment plants have been designed in which biowaste is sterilized prior to conducting to the sewer system. The sterilization of biowaste can be carried out chemically or by means of heat. The treatment plants can operate continuously or batchwise.

Sterilization in the context of the present discussion includes the killing of microbes including bacteria and viruses so as to render them non-pathogenic, as well as the destruction of other biological agents that may cause harmful effects.

A typical thermal continuous biowaste sterilisation apparatus comprises a separating unit for solid matter, a storage tank, a heating unit and a dwell circuit as well as a circulation circuit for circulating biowaste through said heating unit and said dwell circuit.

Separation of solid matter from a biowaste suspension or slurry is necessary in order not to cause clogging of the system or excessive scaling of heat transfer surfaces. Biowaste slurries may contain considerable amounts of solids. As the separated solids also constitute a biological hazard, they must be separately and reliably sterilized, by way of e.g. heat treatment, before being disposed of.

SUMMARY OF THE INVENTION

According to the present invention, a device is provided for the reliable separation and sterilization of solids of a given dimension from a biowaste slurry. The device comprises a chamber with a main inlet port and first and second main outlet ports. A unit for separating solids, preferably a filter or screen unit, is adapted to the first main outlet port so, that liquid leaving the chamber will pass through the solids separating unit. A second outlet port is provided directly from the chamber to allow removal of solids collected in the chamber. Means for temperature measurement are provided at representative locations to ensure that sterilizing conditions have been reached in all parts of the solids contained in the device. Preferably, such means comprise temperature sensors connected to a control system.

During operation, solids are separated from the feed stream and remain in the chamber. In the case the separation device is a filter or screen, it is preferably periodically back flushed using steam to ensure sufficient throughput. When the chamber capacity is reached, the feed is stopped, valves are set to appropriate positions and the collected batch of solids is sterilized within the chamber, preferably using heat treatment. Discharge of the sterilized solids takes place through the second main outlet port.

According to a further embodiment of the invention, the mechanical separation device is a cyclone.

According to a second aspect of the present invention, a method is provided for separating solid material from a biowaste suspension and subsequently sterilizing said solid material, comprising the steps of conducting a suspension of biowaste into a chamber, conducting the suspension out of the chamber through a mechanical separation device thereby separating solid particles from the suspension, essentially draining the liquid part of the suspension from the chamber, raising the temperature of the solid material remaining in the chamber by means of direct steam injection to a predetermined sterilization temperature, maintaining said sterilization temperature for a predetermined period of time, and removing the sterilized solid material from the chamber.

The addition of a base to the material to be sterilized may be used as a supplement to steam injection. Examples are alkali metal hydroxides.

Preferably, the sterilized solid material is cooled and the chamber flushed in connection with the removal step.

BRIEF DESCRIPTION OF THE DRAWING

FIG. 1 is a sectional side view of a device according to the invention.

DETAILED DESCRIPTION OF PREFERRED EMBODIMENT

The invention will now be described in detail with reference to the accompanying drawing. In FIG. 1 is shown a sectional side view of a device 1 in accordance with the invention. Chamber 2 is provided with main inlet port 3, first main outlet port 4 and second main outlet port 5. These are fitted with valves. A control system, not shown, is normally provided for controlling and monitoring the operation of the device.

During operation, biowaste slurry is fed into the chamber through main inlet port 3, preferably by pumping. The valve on second main outlet port 5 is closed, and liquid is forced through filter or screen unit 6 and leaves through first main outlet port 4, whose outlet valve is open. The filter or screen unit 6 is dimensioned to retain solid particles according to required specifications. For example, the filter may be designed to retain particles of more than 1 mm diameter. The filter is of a type withstanding sterilization temperatures repeatedly without replacement need. The chamber is a pressure vessel preferably rated for at least 3.1 bar pressure and at least +144° C. temperature. Pressure and/or temperature ratings are dependent on the required sterilization temperature set point.

The filtered phase may be collected in a buffer tank for further heat treatment in a plant as disclosed in e.g. European Patent 1 440 040.

To keep the filter unit open, steam may be periodically supplied through connection 7 with a pressure sufficient to detach a filter cake possibly forming on the upstream filter surface. Intervals of 1 to 5 minutes with a flushing period of 5-30 seconds may be used. A level indicator (not shown) may be used to monitor the need for back flushing.

The filter unit and chamber are dimensioned to separate and hold a volume of solids determined by the capacity requirements of the heat treatment plant. For example, a chamber of about 30 l operational volume may be used. The point when the capacity of the chamber has been reached may be indicated by level switch 8. Subsequently, the valves of the main inlet port 3 and main outlet ports 4, 5 are closed. A sterilization operation may then be carried out, preferably under the supervision of the control system. A sterilization temperature set point and exposure period are set, e.g. 130° C. for 20 minutes.

Sterilization steam (e.g. plant steam at 2.5 bar supply pressure) is supplied both through the filter 6 via connection 7 and through the lowest point of the chamber via connection 9 on a branch of second main outlet port 5. Condensate leaves through outlet port 10, preferably connected to the buffer tank of the downstream heat treatment plant, thus ensuring proper sterilization also of any entrained material.

The sterilization temperature is monitored using a measurement sensor 12 at connection 9, and coldest point measurement 13 at the far end of the condensate line. Both of the sensor readings must be above the set temperature for the sterilization conditions to be accepted by the control system. When both temperature sensors have reached set point, the sterilization exposure period begins. Preferably, the first sensor is located at the bottom of the solid load and the second is located close to the steam trap in the outlet pipe to provide a representative result for sterilization, showing that the required temperature has been reached throughout the load. The sterilization process can be validated by a microbiological challenge test using e.g. *Geobacillus Stearothermophilus* spores in a sterilization sequence, to prove an overkill result of min. $10^6$ population reduction.

After the exposure period, the program of the control system proceeds to a cooling step. During this step, all valves remain closed and steam supply is stopped. The program waits for the temperatures at both measuring points to fall e.g. below +90° C.

When a temperature of +90° C. is reached, the program proceeds to an emptying and rinse-discharge step. During this step, the second main outlet port 5 functions as a solids discharge port. The valve of second main outlet port 5 is opened and the valve on rinse water inlet 11 opens, e.g. for a period of 60 to 120 seconds, to clean the chamber and to convey all of the decontaminated solids through the second main outlet port to the drain.

Advantageously, a spool piece 14 is adapted in the filtrate discharge line to facilitate service and replacement of the filter unit. Removal of the spool piece allows removal of the filter through outlet port 4.

Advantageously, two units may be connected in parallel to maintain continuous operation if one unit reaches maximum capacity and proceeds to the sterilization and discharge steps.

The sterilization of solid material by injection of steam directly into the material is highly efficient compared to the heating of a volume of liquid in which the corresponding material is suspended.

The above detailed description is to be taken as an example, not limiting the invention relative to the patent claims.

Having described the invention, the following is claimed:

1. A separation and sterilization device for separating batches of solid material from a liquid slurry including biologically hazardous material and for sterilizing separated solid materials, said device comprising:
    a pressure vessel defining a chamber for receiving said slurry;
    a main valved inlet port fluidically connected to said chamber for feeding said slurry into said chamber;
    a first main outlet port fluidically connected to said chamber;
    a filter for separating solid material in said slurry from liquid in said slurry, said filter being disposed between said first main outlet port and said main valved inlet port such that said liquid in said slurry passes through said filter and is discharged through said first main outlet port into a valved filtrate discharge line fluidically connected thereto, said valved discharge line having a first steam inlet in fluid communication therewith;
    a second main valved outlet port disposed upstream of said filter, at a location between said main valved inlet port and said filter, for discharging said solid material from said chamber and allowing fluid to exit the chamber during a sterilization process, said second main valved outlet port including a first temperature sensor and a second steam inlet in fluid communication therewith;
    a spool piece in the filtrate discharge line to facilitate service and replacement of the filter, wherein removal of the spool piece allows removal of the filter through said first main outlet port; and
    a condensate line in fluid communication with said chamber to permit condensate to exit said chamber, said condensate line including a second temperature sensor.

2. A device according to claim 1, further comprising:
    a rinse water inlet for conveying rinse water into said chamber, said rinse water inlet disposed upstream of said filter, at a location between said main valved inlet port and said filter.

3. A device according to claim 1, wherein said filter is a screen.

4. A device according to claim 1, further comprising:
    a level switch for indicating when the capacity of the chamber has been reached.

\* \* \* \* \*